United States Patent [19]

Fox

[11] Patent Number: 4,485,227

[45] Date of Patent: Nov. 27, 1984

[54] BIOCOMPATIBLE POLY-(ETHER-URETHANE-UREA) AND PROCESS FOR ITS PREPARATION

[75] Inventor: Adrian S. Fox, Waterford, Conn.

[73] Assignee: Howmedica, Inc., New York, N.Y.

[21] Appl. No.: 505,130

[22] Filed: Jun. 16, 1983

[51] Int. Cl.³ .............................................. C08G 18/38
[52] U.S. Cl. ............................................... 528/61; 3/1
[58] Field of Search ............................ 528/61; 3/1 A

[56] References Cited

U.S. PATENT DOCUMENTS 4,173,689 8/1979 Lyman .................................... 521/64

Primary Examiner—Maurice J. Welsh
Attorney, Agent, or Firm—Charles J. Knuth; Peter C. Richardson; Harold W. Ordway

[57] ABSTRACT

An improved biocompatible and hemocompatible segmented poly-(ether-urethane-urea) is prepared by a process which comprises condensing an alkylene polyether diol of molecular weight of 500 to 6000 with substantially two equivalents of an aryl, aralkyl, or alkyl diisocyanate of 6 to 20 carbon atoms; condensing the thus-formed α,Ω-diisocyanato poly-(ether-urethane) with a substantially equivalent proportion of a primary alkyl diamine of 2 to 6 carbon atoms until a degree of condensation of about 5 to 20 is achieved; condensing the resulting poly-(ether-urethane-urea) with a primary alkyl amine or diamine of up to 6 carbon atoms in an amount substantially equivalent to the free isocyanate content of the poly-(ether-urethane-urea); and condensing the amine-treated poly-(ether-urethane-urea) with an amine-reacting agent in an amount substantially equivalent to the free amine content of the amine-treated poly-(ether-urethane-urea). The polymer is especially suitable for fabricating replacements for damaged cardiovascular and urinary tract vessels.

16 Claims, No Drawings

BIOCOMPATIBLE POLY-(ETHER-URETHANE-UREA) AND PROCESS FOR ITS PREPARATION

BACKGROUND OF THE INVENTION

This invention concerns an improved biocompatible and hemocompatible poly-(ether-urethane-urea) and a process for its preparation.

The need for suitable materials from which to fabricate prostheses such as cardiovascular and urinary tract implants as substitutes for damaged human and animal tissue continues to exist. Of special import is the need for a material other than autogenous tissue such as the saphenous vein to replace damaged veins and small diameter arteries.

Urethane elastomers, because of their excellent strength, tear, abrasion and oil resistance properties as well as their variety in structure, early found a large number of prosthetic uses. Of particular significance today are the linear block poly-(ether-urethane-ureas) in which a polyether diol is reacted with a diisocyanate and the resultant product is chain extended by reaction with a diamine. While such copolymers have been adapted for use in cardiovascular devices as described, for example, in U.S. Pat. No. 4,173,689, their sensitivity to discoloration in both the solid and solution form upon prolonged exposure to light and the tendency of solutions of the polymers to gel on standing limit their usefulness.

It is therefore a primary objective of the present invention to provide a modified poly-(ether-urethane-urea) which does not possess such shortcomings.

SUMMARY OF THE INVENTION

It has now been found that the capping of reactive end groups of a poly-(ether-urethane-urea) results in a more useful form of the block copolymer.

The present invention therefore entails a biocompatible and hemocompatible segmented poly-(ether-urethane-urea) of the formula I:

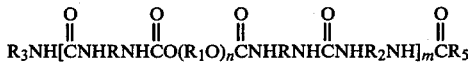

wherein
- R = arylene, aralkylene or alkylene each having from 6 to 20 carbons,
- $R_1$ = alkylene having from 2 to 6 carbons,
- $R_2$ = alkylene having from 2 to 6 carbons,
- $R_3$ = alkyl having up to 4 carbons or $R_5CONHR_4$ or $R_6NHCONHR_4$ wherein
- $R_4$ = alkylene having from 2 to 6 carbons,
- $R_5$ = aryl or alkyl each having up to 16 carbons and
- $R_6$ = aryl or alkyl each having up to 12 carbons,
- n = a number from about 7 to 35, and
- m = a number from about 5 to 20.

The poly-(ether-urethane-urea) is preferably one wherein R=4,4'-diphenylmethane; $R_1$=1-methyl ethylene; $R_2$=ethylene; $R_3$=$R_5CONHR_4$; $R_4$=ethylene; $R_5$=methyl; n=from about 13 to 15; and m=from about 8 to 16.

The present invention also entails a process for the preparation of a biocompatible and hemocompatible segmented poly-(ether-urethane-urea), which comprises:

(a) condensing an alkylene polyether diol of molecular weight of from about 500 to 6000 with substantially two equivalents of an aryl, aralkyl, or alkyl diisocyanate each of from 6 to 20 carbon atoms;

(b) condensing the thus-formed α,Ω-diisocyanato poly-(ether-urethane) with a substantially equivalent proportion of a primary alkyl diamine of from 2 to 6 carbon atoms until a degree of condensation of from about 5 to 20 is achieved;

(c) condensing the resulting poly-(ether-urethane-urea) with a primary alkyl amine of up to 6 carbon atoms in an amount substantially equivalent to the free isocyanate content of the poly-(ether-urethane-urea); and (d) condensing the resulting amine-treated poly-(ether-urethane-urea) with an amine-reacting agent in an amount substantially equivalent to the free amine content of the amine-treated poly-(ether-urethane-urea).

Preferably, the diol is selected from polyethylene glycol, poly-(1,2-propylene glycol) and poly-(1,4-butylene glycol); the diisocyanate is selected from 4,4'-diphenylmethane diisocyanate, toluene 2,4-diisocyanate, 2,2,4-trimethylhexamethylene diisocyanate and isophorone diisocyanate; the primary alkyl amine is a monoamine of from 1 to 4 carbons or a diamine of from 2 to 6 carbons; and the amine-reacting agent is selected from aryl or alkyl acid anhydrides, acid chlorides and monoisocyanates of up to 16 carbon atoms.

The condensations are preferably conducted in a nonreactive, aprotic, water-miscible solvent, with the temperature of the condensations from about 60° to 100° C. in step (a), from about 15° to 30° C. in steps (b) and (c) and from about 20° to 80° C. in step (d).

The alkylene polyether diol may include up to about 15 mole percent of an alkylene triol of from 3 to 8 carbon atoms, or up to about 50 mole percent of an unsaturated alkylene diol of from 6 to 12 carbon atoms.

An especially suitable process for preparing the segmented poly-(ether-urethane-urea) comprises (a) contacting poly-(1,2-propylene glycol) of nominal molecular weight of 950 to 1050 with substantially two equivalents of 4,4'-diphenylmethane diisocyanate in dimethyl sulfoxide/diglyme solvent at a temperature of from about 80° to 85° C.; (b) contacting the thus-formed α,Ω-diisocyanato poly-(ether-urethane) with a substantially equivalent proportion of ethylenediamine in the same solvent at a temperaure of from about 25° to 30° C.; (c) contacting the resulting poly-(ether-urethane-urea) in the solvent at a temperature of from about 20° to 25° C. with about 8 mole percent additional ethylenediamine; and (d) contacting the amine-treated poly-(ether-urethane-urea) in the solvent at a temperature of from about 20° to 60° C. with about 16 mole percent acetic anhydride.

The present invention further entails a method of repairing a duct in a living body which comprises replacing the defective portion of the duct with its equivalent in size and shape fabricated from the disclosed poly-(ether-urethane-urea), especially where the duct is a blood vessel, a ureter or a urethra.

DETAILED DESCRIPTION OF THE INVENTION

The improved polymer of the present invention, in which a poly-(ether-urethane-urea) with reactive end groups has been capped to render the end groups inert, is a more useful form of the polymer with exceptional application in the development of cardiovascular, urinary tract and orthopaedic implants.

In preparing the instant polymer, an alkylene polyether diol having a molecular weight of from about 500 to 6000 is condensed with substantially two equivalents of an aryl, arakyl, or alkyl diisocyanate of from 6 to 20 carbon atoms. The diol is preferably selected from poly-(ethylene glycol), poly-(propylene-1,2-glycol), poly-(propylene-1,3-glycol), poly-(tetramethylene-1,4-glycol), poly-(pentamethylene-1,5-glycol), and poly-(hexamethylene-1,6-glycol), poly-(propylene-1,2-glycol) of nominal molecular weight 950 to 1050 being especially preferred. The diisocyanate is preferably selected from toluene 2,4-diisocyanate, 2,2,4-trimethylhexamethylene diisocyanate, isophorone diisocyanate, and especially 4,4'-diphenylmethane diisocyanate. This and the subsequent condensations are preferably conducted in a nonreactive, aprotic, water-miscible solvent such as N-methylpyrrolidone, N-methylmorpholine, dimethylacetamide, dimethylformamide, tetramethylene sulfone, dimethyl sulfoxide, dioxane, tetrahydrofuran, 1,2-dimethoxyethane, bis-(2-methoxyethyl ether)-(diglyme), ethylene glycol diethyl ether, diethylene glycol dimethyl ether, triethylene glycol dimethyl ether, and diethylene glycol diethyl ether. The temperature of this initial condensation is preferably from about 60° to 100° C., a reaction temperature of from about 80° to 85° C. in a dimethyl sulfoxide/diglyme solvent being especially preferred.

The thus-formed $\alpha,\Omega$-diisocyanato poly-(ether-urethane) is then condensed with a substantially equivalent proportion of a primary alkyl diamine of from 2 to 6 carbon atoms, preferably at a temperature of from about 15° to 30° C., until a degree of condensation of from about 5 to 20 is achieved. Preferably the diamine is 1,2-diaminoethane (ethylenediamine), 1,3-diaminopropane, 1,4-hexamethylenediamine, 2,2'-Bis-(aminoethyl) ether, 1,5-pentamethylenediamine or 1,6-hexamethylenediamine, condensation at from about 25° to 30° C. with ethylenediamine being especially preferred.

The resulting poly-(ether-urethane-urea) is then condensed with a primary alkyl amine of up to 6 carbon atoms in an amount substantially equivalent to its free, or reactive, isocyanate content. The primary alkyl amine may be a monoamine of from 1 to 4 carbons or a diamine of from 2 to 6 carbons. Preferably the condensation is conducted at from about 15° to 30° C., condensation with about 8 mole percent additional ethylenediamine at about 20° to 25° C. being especially preferred.

Finally, the amine-treated poly-(ether-urethane-urea) is condensed with an amine-reacting agent in an amount substantially equivalent to its free, or reactive, amine content. Preferably, the amine-reacting agent is selected from aryl or alkyl acid anhydrides, acid chlorides and mono isocyanates of up to 16 carbon atoms. The condensation is preferably conducted at a temperature from about 20° to 80° C., condensation with about 16 mole percent acetic anhydride and at a temperature of from about 20° to 60° C. being especially preferred.

In alternative versions of the polymerization, the alkylene polyether diol may include up to about 15 mole percent of an alkylene triol of from 3 to 8 carbon atoms, based on the total polyol charged, to increase the apparent molecular weight and therefore the melt or solution viscosity of the polymer, or up to about 50 mole percent of an unsaturated alkylene diol of from 6 to 12 carbon atoms, based on the total polyol charged, to control the stiffness of the polymer. Preferably, the alkylene triol is selected from trimethylolpropane, penetaerythritol monomethyl ether and glycerol, while the unsaturated alkylene diol is selected from tri-methylolpropane monoallyl ether, pentaerythritol diallyl ether and glycerol monoallyl ether.

The novel poly-(ether-urethane-urea) of the present invention is readily converted to implantable biomedical devices by established techniques such as extrusion, injection molding and dip casting. An especially preferred method is that disclosed in U.S. Pat. No. 4,173,689, the contents of which is incorporated herein by reference. Such implantable devices include small diameter blood vessels, nerve and tendon sheathing, A/V shunts, ureters and urethras.

The following examples are merely illustrative and are not to be construed as limiting the invention, the scope of which is defined by the appended claims.

EXAMPLE 1

Into a 5-liter Morton type resin kettle fitted with a fixed blade stainless steel agitator and shaft, high torque agitator motor, gas inlet tube, Allyn condensor, immersion thermometer and heating mantle, and protected from the atmosphere with fresh ⅛-inch 3 Angstrom molecular sieves, was placed 758.8 g (0.75 mole) of poly-(1,2-proplene glycol), approximate molecular weight 1025[1], predried by vacuum stripping on a rotary evaporator at 60° C. for 3 hours at a pressure of less than 0.5 mm Hg; 1375 ml of diglyme (bis-(2-methoxyethyl)ether)[2] distilled from calcium hydride; and 1000 ml of dimethyl sulfoxide[3]. Under a general nitrogen purge and with agitation, 375.4 g (1.5moles) of freshly distilled, flaked 4,4'-diphenylmethane diisocyanate[4] was washed into the flask from a dry powdered funnel with 375 ml of dimethyl sulfoxide.

The reaction mixture was stirred under the nitrogen atmosphere for 1.75 hours at 85° C.

The heating mantle was then replaced by an ice bath, and the reaction mixture solution was cooled under continued agitation and nitrogen purging to 20° C. A solution of 45.1 g (0.75 mole) of fresh distilled ethylenediamine[5] and 500 ml of dimethyl sulfoxide was quickly added to the reaction mixture. An additional 60 ml of dimethyl sulfoxide was used to rinse the funnel containing the diamine into the kettle. The viscosity and temperature of the reaction mixture increased very rapidly, the temperature rising to about 36° C.; one hour after the diamine addition, the temperature in the kettle had cooled back to 20° C.

A solution of 3.54 g (0.06 mole) of ethylenediamine and 25 ml of dimethyl sulfoxide was quickly added to the stirred, viscous reaction mixture. About 30 minutes later, the ice bath was removed from the kettle and a solution of 12.05 g (0.12 mole) of reagent grade acetic anhydride[5] dissolved in 5 ml dimethyl sulfoxide was added. The heating mantle was replaced around the kettle, and the reaction mixture was warmed to 60° C., under agitation and nitrogen purging, and stirred an additional 30 minutes at that temperature.

The polymer was coagulated by adding approximately 500 ml aliquots of the polymer solution to 2500 ml of deionized water in a stainless steel Waring blender. After completion of the coagulation, the polymer crumb was filtered and washed twice more with deionized water in the blender to remove traces of solvents and water-soluble reactants. The polymer was air dried for 24 hours and then vacuum dried for 72 hours at 50° C., 0.5 mm Hg.

The polymer so produced was obtained in 97% yield and had the following properties: Solution viscosity 2,920 cps (20 wt.% in DMSO, 25° C., Brookfield); $\overline{M}_W$ 46,760, $\overline{M}_N$ 24,580, $\overline{M}_W/\overline{M}_N$ 1.90 (GPC-DMF, 25° C.); $T_{1\% \ wt. \ loss}$ 247° C.

[1] NIAX® Polyol PPG-1025; Union Carbide Corporation, Danbury, CT
[2] Aldrich Chemical Co., Inc., Milwaukee, WI
[3] DMSO, distilled-in-glass, grade; Burdick and Jackson Laboratories, Inc., Muskegon, MI
[4] MONDUR M; Mobay Chemical Corporation, Pittsburgh, PA
[5] J. T. Baker Chemical Co., Phillipsburg, NJ

EXAMPLE 2

The reaction and isolation procedures of Example 1 are repeated with the following reactants and amounts: 602.3 g (0.595 mole) poly-(1,2-propylene glycol), 58.96 g (0.37 mole) trimethylolpropane monoallyl ether[1], and 482.18 g (1.927 moles) 4,4'-diphenylmethane diisocyanate in initial condensation reaction at 85° C.; 57.88 g (0.963 mole) ethylenediamine in second condensation reaction at 20°–36° C.; 4.55 g (0.077 mole) ethylenediamine in initial capping reaction at 20° C.; and 15.47 g (0.154 mole) acetic anhydride in the final capping reaction at 60° C. An isolated and dried polymer having apparent molecular weights and solution viscosity properties similar to those of the polymer of Example 1 and showing a considerable increase in modulus of rupture upon radiation (2.5 Mrad) sterilization is obtained.

[1] Celanese Plastics and Specialties Co., Chatham, NJ

EXAMPLE 3

The reaction and isolation procedures of Example 1 are repeated with the following reactants and amounts: 683.1 g (0.675 mole) poly-(1,2-propylene glycol), 9.01 g (0.067 mole) trimethylolpropane[1], and 394.15 g (1.575 moles) 4,4'-diphenylmethane diisocyanate in initial condensation reaction at 85° C.; 47.33 g (0.788 mole) ethylenediamine in second condensation reaction at 20°–36° C.; 3.54 g (0.06 mole) ethylenediamine in initial capping reaction at 20° C.; and 12.05 g (0.12 mole) acetic anhydride in final capping reaction at 60° C. An isolated and dried polymer having about 10 percent branching and with higher apparent molecular weight and solution viscosity properties than those of the polymer of Example 1 is obtained.

[1] Aldrich Chemical Co.

I claim:

1. A biocompatible and hemocompatible segmented poly-(ether-urethane-urea) of the formula I:

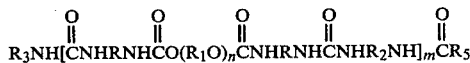
                                                     I wherein
   R = arylene, aralkylene or alkylene each having from 6 to 20 carbons,
   $R_1$ = alkylene having from 2 to 6 carbons,
   $R_2$ = alkylene having from 2 to 6 carbons,
   $R_3$ = alkyl having up to 4 carbons or $R_5CONHR_4$ or $R_6NHCONHR_4$ wherein
   $R_4$ = alkylene having from 2 to 6 carbons,
   $R_5$ = aryl or alkyl each having up to 16 carbons and
   $R_6$ = aryl or alkyl each hving up to 12 carbons,
   n = a number from about 7 to 35, and
   m = a number from about 5 to 20.

2. The poly-(ether-urethane-urea) of claim 1 wherein R = 4,4'-diphenylmethane; $R_1$ = 1-methyl ethylene; $R_2$ = ethylene; $R_3$ = $R_5CONHR_4$; $R_4$ = ethylene; $R_5$ = methyl; n = from about 13 to 15; and m = from about 8 to 16.

3. A process for the preparation of a biocompatible and hemocompatible segmented poly-(ether-urethane-urea), which comprises:
   (a) condensing an alkylene polyether diol of molecular weight of from about 500 to 6000 with substantially two equivalents of an aryl, aralkyl, or alkyl diisocyanate each of from 6 to 20 carbon atoms;
   (b) condensing the thus-formed α,Ω-diisocyanato poly-(ether-urethane) with a substantially equivalent proportion of a primary alkyl diamine of from 2 to 6 carbon atoms until a degree of condensation of from about 5 to 20 is achieved;
   (c) condensing the resulting poly-(ether-urethane-urea) with a primary alkyl amine of up to 6 carbon atoms in an amount substantially equivalent to the free isocyanate content of said poly-(ether-urethane-urea); and
   (d) condensing the resulting amine-treated poly-(ether-urethane-urea) with an amine-reacting agent in an amount substantially equivalent to the free amine content of said amine-treated poly-(ether-urethane-urea).

4. The process of claim 3 wherein said diol is selected from the group consisting of polyethylene glycol, poly-(1,2-propylene glycol) and poly-(1,4-butylene glycol).

5. The process of claim 3 wherein said diisocyanate is selected from the group consisting of 4,4'-diphenylmethane diisocyanate, toluene 2,4-diisocyanate, 2,2,4-trimethylhexamethylene diisocyanate and isophorone diisocyanate.

6. The process of claim 3 wherein said primary alkyl amine is a monoamine of from 1 to 4 carbons or a diamine of from 2 to 6 carbons.

7. The process of claim 3 wherein said amine-reacting agent is selected from the group consisting of aryl or alkyl acid anhydrides, acid chlorides and monoisocyanates of up to 16 carbon atoms.

8. The process of claim 3 wherein said condensations are conducted in nonreactive, aprotic, water-miscible solvent.

9. The process of claim 8 wherein the temperature of said condensations is from about 60° to 100° C. in step (a), from about 15° to 30° C. in steps (b) and (c) and from about 20° to 80° C. in step (d).

10. The process of claim 3 wherein said diol includes up to about 15 mole percent of an alkylene triol of from 3 to 8 carbon atoms.

11. The process of claim 3 wherein said diol includes up to about 50 mole percent of an unsaturated alkylene diol of from 6 to 12 carbon atoms.

12. The segmented poly-(ether-urethane-urea) of the process of claim 3.

13. A process for preparing a biocompatible and hemocompatible segmented poly-(ether-urethane-urea), which comprises:
   (a) contacting poly-(1,2-propylene glycol) of nominal molecular weight of 950 to 1050 with substantially two equivalents of 4,4'-diphenylmethane diisocyanate in dimethyl sulfoxide/diglyme solvent at a temperature of from about 80° to 85° C.;
   (b) contacting the thus-formed α,Ω-diisocyanato poly-(ether-urethane) with a substantially equivalent proportion of ethylenediamine in said solvent at a temperature of from about 25° to 30° C.;
   (c) contacting the resulting poly-(ether-urethane-urea) in said solvent at a temperature of from about 20° to 25° C. with about 8 mole percent additional ethylenediamine; and (d) contacting the amine-treated poly-(ether-urethane-urea) in said solvent at a temperature of from about 20° to 60° C. with about 16 mole percent acetic anhydride.

14. The segmented poly-(ether-urethane-urea) of the process of claim 13.

15. A method of repairing a duct in a living body, which comprises replacing the defective portion of said duct with its equivalent in size and shape fabricated from the poly-(ether-urethane-urea) of claim 1.

16. The method of claim 15 wherein said duct is a blood vessel, a ureter or a urethra.

* * * * *